(12) United States Patent
Nguyen et al.

(10) Patent No.: US 9,204,665 B2
(45) Date of Patent: Dec. 8, 2015

(54) ELECTRON FLOW GENERATION

(76) Inventors: Cattien Van Nguyen, San Jose, CA
(US); Bryan P. Ribaya, San Jose, CA
(US)

(*) Notice: Subject to any disclaimer, the term of this patent is extended or adjusted under 35 U.S.C. 154(b) by 667 days.

(21) Appl. No.: 13/288,838

(22) Filed: Nov. 3, 2011

(65) Prior Publication Data

US 2012/0107465 A1 May 3, 2012

Related U.S. Application Data

(60) Provisional application No. 61/409,889, filed on Nov. 3, 2010.

(51) Int. Cl.
*A23L 3/26* (2006.01)
*A23L 3/32* (2006.01)
*B82Y 30/00* (2011.01)
*G21K 5/02* (2006.01)
*H01J 33/04* (2006.01)
*A61L 2/08* (2006.01)

(52) U.S. Cl.
CPC ... *A23L 3/26* (2013.01); *A23L 3/32* (2013.01); *B82Y 30/00* (2013.01); *G21K 5/02* (2013.01); *H01J 33/04* (2013.01); *A61L 2/087* (2013.01)

(58) Field of Classification Search
CPC ............ A61L 2/087; A23L 3/26; A23L 3/32; B82Y 30/00; G21K 5/02; H01J 33/04
USPC .......................................... 422/240; 977/902
See application file for complete search history.

(56) References Cited

U.S. PATENT DOCUMENTS

| | | | |
|---|---|---|---|
| 6,097,138 A * | 8/2000 | Nakamoto | 313/309 |
| 6,140,657 A | 10/2000 | Wakalopulos et al. | |
| 6,650,061 B1 * | 11/2003 | Urayama et al. | 315/169.3 |
| 7,078,716 B2 | 7/2006 | Fink et al. | |
| 7,220,971 B1 * | 5/2007 | Chang et al. | 250/398 |
| 7,548,018 B2 | 6/2009 | Lee | |
| 2004/0195950 A1 * | 10/2004 | Ryu et al. | 313/311 |
| 2004/0227447 A1 * | 11/2004 | Yaniv et al. | 313/309 |
| 2005/0184648 A1 * | 8/2005 | Chi et al. | 313/497 |

FOREIGN PATENT DOCUMENTS

| | | |
|---|---|---|
| JP | 2002304961 | 10/2002 |
| JP | 2005251502 | 9/2005 |

* cited by examiner

*Primary Examiner* — Regina M Yoo (57) ABSTRACT

An apparatus, system and method of using electrons to perform at least one operation are disclosed. An apparatus may include groups of carbon nanotubes capable of emitting a relatively large number of electrons for use in performing operations such as sterilization, purification, deodorization, cleaning, cross-linking, pest control, pathogen control, chain-scissioning associated with surface modification, waste treatment, etc. Each group of carbon nanotubes may be aligned with a respective opening in a member, where the member may be coupled with a membrane capable of transmitting electrons. Electrons may be emitted from the carbon nanotubes by applying a vacuum to the carbon nanotubes and also applying an electric potential between the carbon nanotubes and the member. As such, electrons from a plurality of groups of carbon nanotubes may generate an electron flow that can be used to perform one or more operations on a fluid, object, or other type of component.

15 Claims, 8 Drawing Sheets

ELECTRON FLOW GENERATION

RELATED APPLICATIONS

The present application claims the benefit of U.S. Provisional Patent Application No. 61/409,889, filed Nov. 3, 2010, entitled "ELECTRON BEAM DEVICE WITH CARBON NANOTUBE FIELD EMITTER ARRAY AND ELECTRON TRANSMISSION MEMBRANE ARRAY FOR LOW VOLTAGE OPERATION," naming Cattien Nguyen and Bryan Ribaya as inventors. That application is incorporated herein by reference in its entirety and for all purposes.

BACKGROUND OF THE INVENTION

Electron beam tubes have been used in conventional systems for sterilizing fluids and other materials. For example, as described in U.S. Pat. No. 6,140,657, an electron beam tube can be used to create a plasma cloud used for sterilization. Electrons produced by a single cathode are emitted from a single, large window in the electron beam tube.

However, as taught by U.S. Pat. No. 6,140,657, there are numerous problems with this approach. The number of electrons emitted by conventional systems is low, and therefore, the overall energy of the electron beam is relatively low and unable to penetrate materials to any appreciable depth. Furthermore, conventional systems require placement of the object to be sterilized in a helium-filled and sealed chamber, thereby limiting the types of objects that can be being sterilized.

SUMMARY OF THE INVENTION

Accordingly, a need exists for a system capable of emitting a larger number of electrons for use in sterilization or in other operations. A need also exists for a system capable of performing sterilization or other operations without the use of a helium-filled chamber. Embodiments of the present invention provide novel solutions to these needs and others as described below.

Embodiments of the present invention are directed to an apparatus, system and method of using electrons to perform at least one operation. More specifically, an apparatus may include groups of carbon nanotubes capable of emitting a relatively large number of electrons for use in performing operations such as sterilization, purification, deodorization, cleaning, cross-linking, pest control, pathogen control, chain-scissioning associated with surface modification, waste treatment, etc. Each group of carbon nanotubes may be aligned with a respective opening in a member, where the member may be coupled with a membrane capable of transmitting electrons. Electrons may be emitted from the carbon nanotubes by applying a vacuum to the carbon nanotubes and also applying an electric potential between the carbon nanotubes and the member in one embodiment. As such, electrons from a plurality of groups of carbon nanotubes may generate an electron flow (e.g., passing through openings defined by the member and also passing through the membrane) that can be used to perform one or more operations on a fluid, object, or other type of component.

In one embodiment, an apparatus includes a plurality of groups of carbon nanotubes operable to generate an electron flow. A member is coupled with the plurality of groups of carbon nanotubes, wherein a plurality of openings is defined in the member, and wherein each opening of the plurality of openings is aligned with a respective group of the plurality of groups of carbon nanotubes. The apparatus also includes a membrane disposed on the member and operable to transmit electrons of the electron flow onto a component.

In another embodiment, a system includes a plurality of groups of carbon nanotubes operable to generate an electron flow. A member is coupled with the plurality of groups of carbon nanotubes, wherein a plurality of openings is defined in the member, and wherein each opening of the plurality of openings is aligned with a respective group of the plurality of groups of carbon nanotubes. The apparatus also includes a membrane disposed on the member and operable to transmit electrons of the electron flow onto a component. The system also includes a vacuum source operable to apply a vacuum to the plurality of groups of carbon nanotubes.

In yet another embodiment, a method includes applying a vacuum to a plurality of groups of carbon nanotubes, wherein the plurality of groups of carbon nanotubes is coupled with a member, and wherein each opening of a plurality of openings defined in the member is aligned with a respective group of the plurality of groups of carbon nanotubes. An electric potential is applied between the plurality of groups of carbon nanotubes and the member to generate an electron flow through the plurality of openings. The method also includes introducing a component into the electron flow, wherein electrons of the electron flow are transmitted through a membrane disposed on the member and onto the component.

BRIEF DESCRIPTION OF THE DRAWINGS

The present invention is illustrated by way of example, and not by way of limitation, in the figures of the accompanying drawings and in which like reference numerals refer to similar elements.

DETAILED DESCRIPTION OF THE INVENTION

Reference will now be made in detail to embodiments of the present invention, examples of which are illustrated in the accompanying drawings. While the present invention will be discussed in conjunction with the following embodiments, it will be understood that they are not intended to limit the present invention to these embodiments alone. On the contrary, the present invention is intended to cover alternatives, modifications, and equivalents which may be included with the spirit and scope of the present invention as defined by the appended claims. Furthermore, in the following detailed description of the present invention, numerous specific details are set forth in order to provide a thorough understanding of the present invention. However, embodiments of the present invention may be practiced without these specific details. In other instances, well-known methods, procedures, components, and circuits have not been described in detail so as not to unnecessarily obscure aspects of the present invention.

Notation and Nomenclature

Some portions of the detailed descriptions which follow are presented in terms of procedures, logic blocks, processing and other symbolic representations of operations on data bits within a computer memory. These descriptions and representations are the means used by those skilled in the data processing arts to most effectively convey the substance of their work to others skilled in the art. In the present application, a procedure, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present invention, discussions utilizing the terms such as "accepting," "accessing," "adding," "analyzing," "applying," "assembling," "assigning," "associating," "calculating," "capturing," "combining," "communicating," "comparing," "collecting," "creating," "defining," "depicting," "detecting," "determining," "displaying," "establishing," "executing," "filtering," "generating," "grouping," "identifying," "initiating," "interacting," "introducing," "modifying," "monitoring," "moving," "outputting," "performing," "placing," "presenting," "processing," "programming," "providing," "querying," "ranking," "removing," "repeating," "sampling," "sorting," "storing," "subtracting," "transforming," "using," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the Invention

Figure 1:
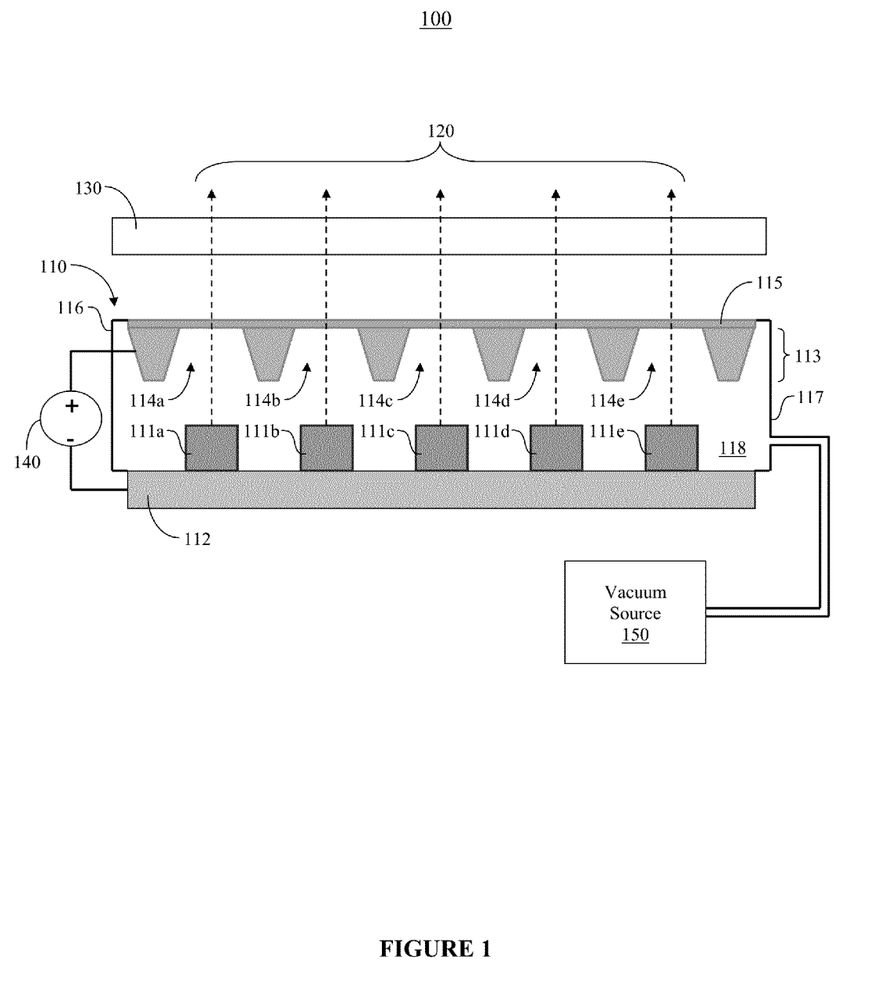
FIG. 1 shows an exemplary system for generating an electron flow in accordance with one embodiment of the present invention.

FIG. 1 shows exemplary system 100 for generating an electron flow in accordance with one embodiment of the present invention. As shown in FIG. 1, electrons flow 120 is emitted from apparatus 110 and directed toward or on component 130. Component 130 may be an object (e.g., a medical supply, food, waste, an object to be cleaned or sterilized by the electrons, a material to be cured by the electrons, another object, etc.), a fluid (e.g., water, paint, another liquid, air, another gas, etc.), etc. Component 130 may be introduced into electron flow 120 (e.g., by moving the component 130 to and/or through electron flow 120, by moving electron flow 120 to and/or through component 130, etc.) to perform one or more operations associated with the component. The one or more operations may include sterilization, purification, deodorization, cleaning, cross-linking (e.g., for curing a paint, ink, coating, adhesive, polymer, etc.), pest control (e.g., in food products, other applications, etc.), pathogen control (e.g., in food products, other applications, etc.), chain-scissioning associated with surface modification, waste treatment, etc. As such, one or more operations may be more effectively performed by using multiple groups of carbon nanotubes to emit electrons.

Additionally, given the increased amount of electrons emitted by the plurality of groups of carbon nanotubes of apparatus 110, component 130 need not be disposed in a helium-filled chamber. For example, component 130 may be disposed in open air, a chamber filled with a fluid other than helium, in an environment of a different pressure than that of the plurality of groups of carbon nanotubes (e.g., within chamber 118), in an environment of the same pressure as that of the plurality of groups of carbon nanotubes (e.g., within chamber 118), etc. Although component 130 need not be disposed in a helium-filled chamber, at least one operation may be performed on component 130 using apparatus 110 while component 130 is disposed in a chamber filled with an inert gas (e.g., such as helium, argon, neon, etc.) in one embodiment.

The electrons of electron flow 120 may be generated by groups of carbon nanotubes (e.g., group 111a, group 111b, group 111c, group 111d, group 111e, etc.). Each group of carbon nanotubes may include a plurality of individual carbon nanotubes. The groups of carbon nanotubes (e.g., group 111a, group 111b, group 111c, group 111d, group 111e, etc.) may be coupled with or grown from substrate 112. And in one embodiment, the groups of carbon nanotubes may be electrically coupled to substrate 112.

As shown in FIG. 1, an electric potential may be applied (e.g., using energy source 140) between the groups of carbon nanotubes (e.g., via substrate 112) and member 113 to cause electron flow 120 to be generated by the groups of carbon nanotubes. Member 113 may be electrically conductive in one embodiment. Each group of carbon nanotubes may be aligned with a respective window or opening (e.g., opening 114a, opening 114b, opening 114c, opening 114d, opening 114e, etc.) defined in member 113. As such, windows or openings defined in member 113 may provide passageways for the electrons to flow from apparatus 110 to object 130.

Figure 2:
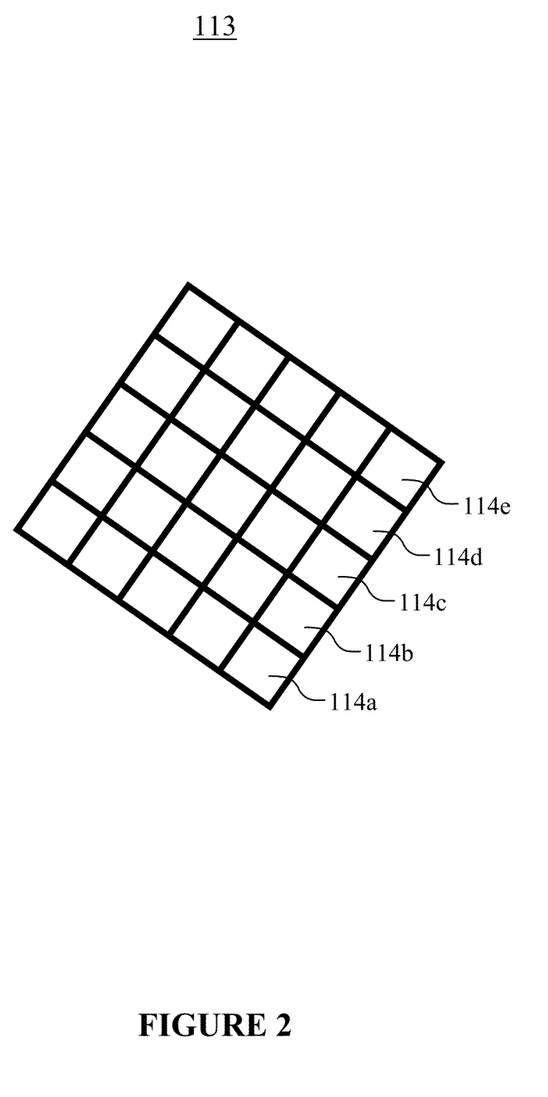
FIG. 2 shows a perspective view of an exemplary member in accordance with one embodiment of the present invention.

FIG. 2 shows a perspective view of exemplary member 113 in accordance with one embodiment of the present invention. As shown in FIG. 2, a plurality of windows or openings may be defined by member 113 to enable the extraction and transmission of electrons from a plurality of groups of carbon nanotubes. The portions of member 113 surrounding each opening may be electrically coupled to one another in one embodiment, thereby allowing extraction of electrons from a plurality of groups of carbon nanotubes with fewer connections (e.g., only one, a few, a smaller number than the number of openings defined in member 113, etc.) to energy source 140.

In one embodiment, the openings defined by member 113 may be approximately 2 inches square. Alternatively, the openings defined by member 113 may be smaller or larger than approximately 2 inches square in other embodiments.

Although FIG. 2 shows member 113 with a specific number of openings defined therein, it should be appreciated that member 113 may have a different number of openings defined therein in other embodiments. Additionally, although member 113 is depicted in FIG. 2 with a specific size and shape, it should be appreciated that member 113 may have different sizes and/or shapes in other embodiments. For example, although FIG. 2 depicts square openings defined in member 113, one or more of the openings may be different shapes (e.g., circles, triangles, another polygon, another shape, etc.) in other embodiments.

Figure 3A:
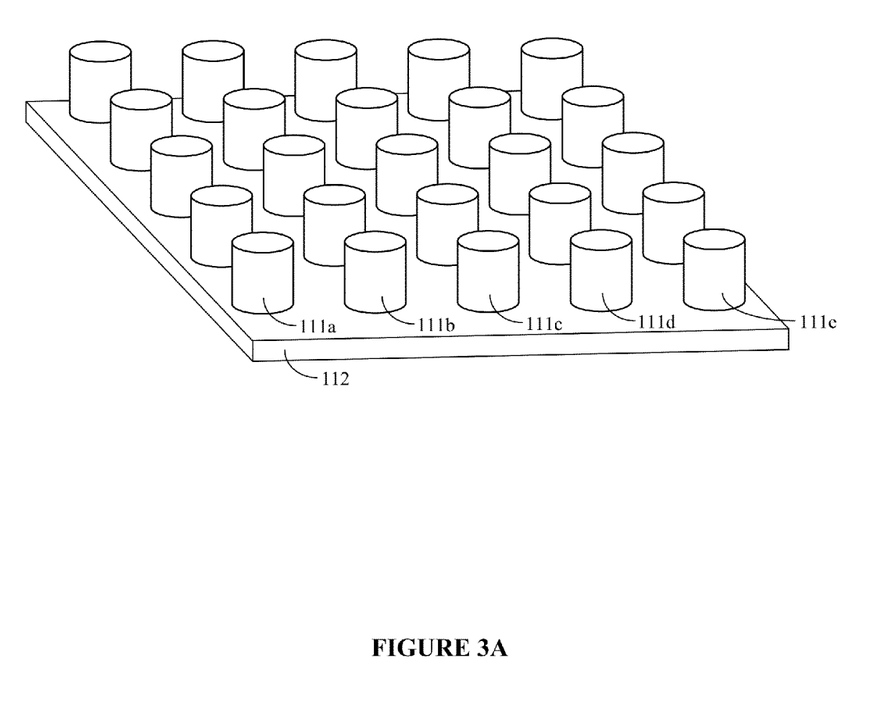
FIG. 3A shows an exemplary arrangement of a plurality of groups of carbon nanotubes in accordance with one embodiment of the present invention.

FIG. 3A shows an exemplary arrangement of a plurality of groups of carbon nanotubes in accordance with one embodiment of the present invention. As shown in FIG. 3A, a plurality of groups of carbon nanotubes (e.g., group 111a, group 111b, group 111c, group 111d, group 111e, etc.) may be coupled with substrate 112. Each group may be spaced apart from (e.g., not touching) one or more other groups of carbon nanotubes. In one embodiment, the plurality of groups of carbon nanotubes may be arranged so that each group of carbon nanotubes is aligned with a respective window or opening (e.g., opening 114a, opening 114b, opening 114c, opening 114d, opening 114e, etc.) defined in member 113 (e.g., as shown in FIG. 1 and/or FIG. 2). As such, a plurality of groups of carbon nanotubes may be utilized to emit a larger number of electrons and/or a higher density of electrons for performing one or more operations (e.g., sterilization, purification, deodorization, cleaning, cross-linking, pest control, pathogen control, chain-scissioning associated with surface modification, waste treatment, etc.) on a component. The electrons may penetrate a surface of the component in one embodiment.

Figure 3B:
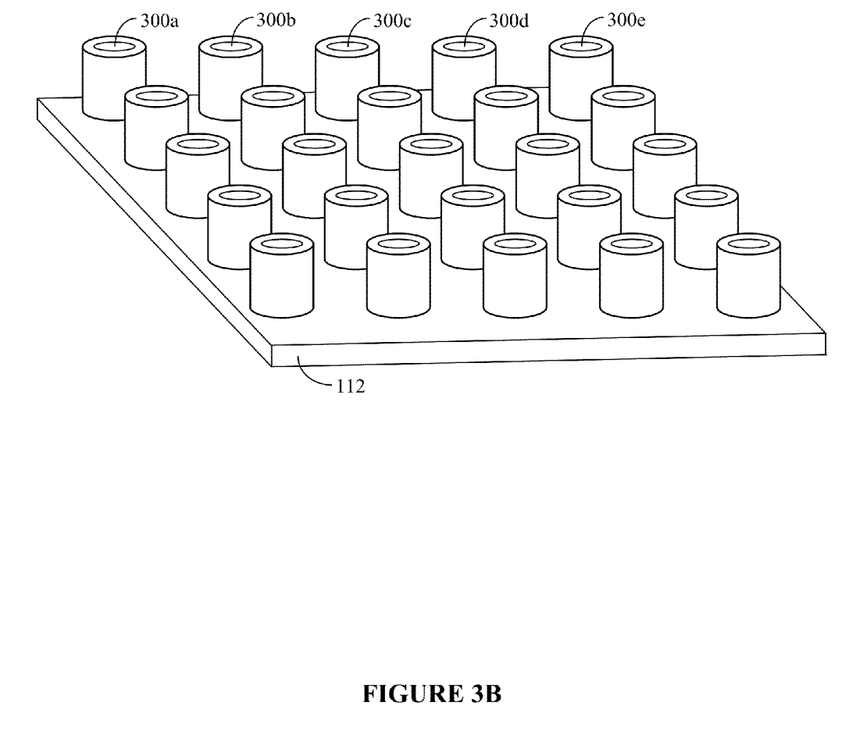
FIG. 3B shows an exemplary arrangement of a plurality of groups of carbon nanotubes defining at least one respective cavity in accordance with one embodiment of the present invention.

As shown in FIG. 3A, one or more groups of carbon nanotubes may be patterned or grown as cylinders. However, it should be appreciated that the groups of carbon nanotubes may have other shapes in other embodiments. For example, one or more groups of carbon nanotubes may be shaped as a prism (e.g., with a cross-section of at least three sides), hemisphere, cone, another shape, etc. As another example, one or more groups of carbon nanotubes may define at least one respective cavity (e.g., 300a, 300b, 300c, 300d, 300e, etc.) as shown in FIG. 3B.

In one embodiment, the shape of the groups of carbon nanotubes may match the shape of the openings defined by member 113. For example, where the openings defined member 113 (e.g., opening 114a, opening 114b, opening 114c, opening 114d, opening 114e, etc.) are circular, the groups of carbon nanotubes may be cylindrical in shape (e.g., as shown in FIG. 3A, with at least one respective cavity defined therein as shown in FIG. 3B, etc.). As another example, where the openings defined member 113 (e.g., opening 114a, opening 114b, opening 114c, opening 114d, opening 114e, etc.) are square (e.g., as shown in FIG. 2), the groups of carbon nanotubes may be shaped like a square prism.

Turning back to FIG. 1, a vacuum may be applied to the groups of carbon nanotubes in one embodiment. For example, where the groups of carbon nanotubes are disposed in chamber 118, vacuum source 150 may apply a vacuum to chamber 118. Chamber 118 may be formed, in one embodiment, by layer or membrane 115, substrate 112, wall 116 and wall 117.

In one embodiment, the vacuum applied to the groups of carbon nanotubes may enable the magnitude of the electric potential (e.g., generated by energy source 140) to be reduced. For example, the magnitude of the electric potential may be approximately 50,000 volts or less (e.g., at any value between approximately 50,000 volts and approximately 500 volts).

Membrane 115 may be electron permeable in one embodiment. For example, membrane 115 may allow electrons (e.g., of electron flow 120) to flow from chamber 118 toward component 130. Membrane 115 may be relatively thin (e.g., less than approximately 10 micrometers, less than approximately 3 micrometers, in the range of approximately 10 nanometers to approximately 10 micrometers, etc.) in one embodiment. Membrane 115 may be made from silicon nitride ($Si_3N_4$), silicon oxide, a combination of silicon nitride and silicon oxide (e.g., at least one silicon nitride layer and at least one silicon oxide layer, a material made of silicon nitride and silicon oxide, etc.), one or more other materials capable of transmitting electrons, etc.

As shown in FIG. 1, member 113 may form a support structure or frame for membrane 115. For example, member 113 may reduce strain or movement of membrane 115 when subjected to stresses (e.g., caused by a vacuum being applied to chamber 118 via vacuum source 150).

In one embodiment, member 113 may be made from any material that is conductive and able to survive in an electron-rich environment. For example, member 113 may be made from one or more metals, one or more conductive polymers, etc.

Substrate 112 may be made from silicon, one or more metals, a metal alloy, a metal or other material capable of growing carbon nanotubes, etc. And in one embodiment, substrate 112 may include a plurality of layers, where the top-most layer (e.g., disposed toward the plurality of groups of carbon nanotubes) may be made from silicon, one or more metals, a metal alloy, a metal or other material capable of growing carbon nanotubes, etc.

Substrate 112 may be approximately parallel with member 113 and/or membrane 115 in one embodiment. Alternatively, substrate 112 may be positioned in another orientation with respect to member 113 and/or membrane 115.

In one embodiment, a filter may be used to remove the by-products or other material produced as a result of the at least one operation associated with component 130. For example, component 130 may be passed through a filter to remove by-products or other material produced as a result of the at least one operation (e.g., sterilization, purification, deodorization, cleaning, etc.). In one embodiment, the filter may be coupled with apparatus 110 and/or connected with a chamber in which component 130 is located.

Although FIG. 1 shows system 100 with a specific number of elements (e.g., groups of carbon nanotubes, members, membranes, openings defined by a member, vacuum sources, energy sources, etc.), it should be appreciated that system 100 may include a different number of elements in other embodiments. Additionally, although FIG. 1 shows system 100 with a specific arrangement and configuration of elements (e.g., groups of carbon nanotubes, members, membranes, openings defined by a member, vacuum sources, energy sources, etc.), it should be appreciated that system 100 may include a different arrangement and/or configuration of elements in other embodiments.

Figure 4:
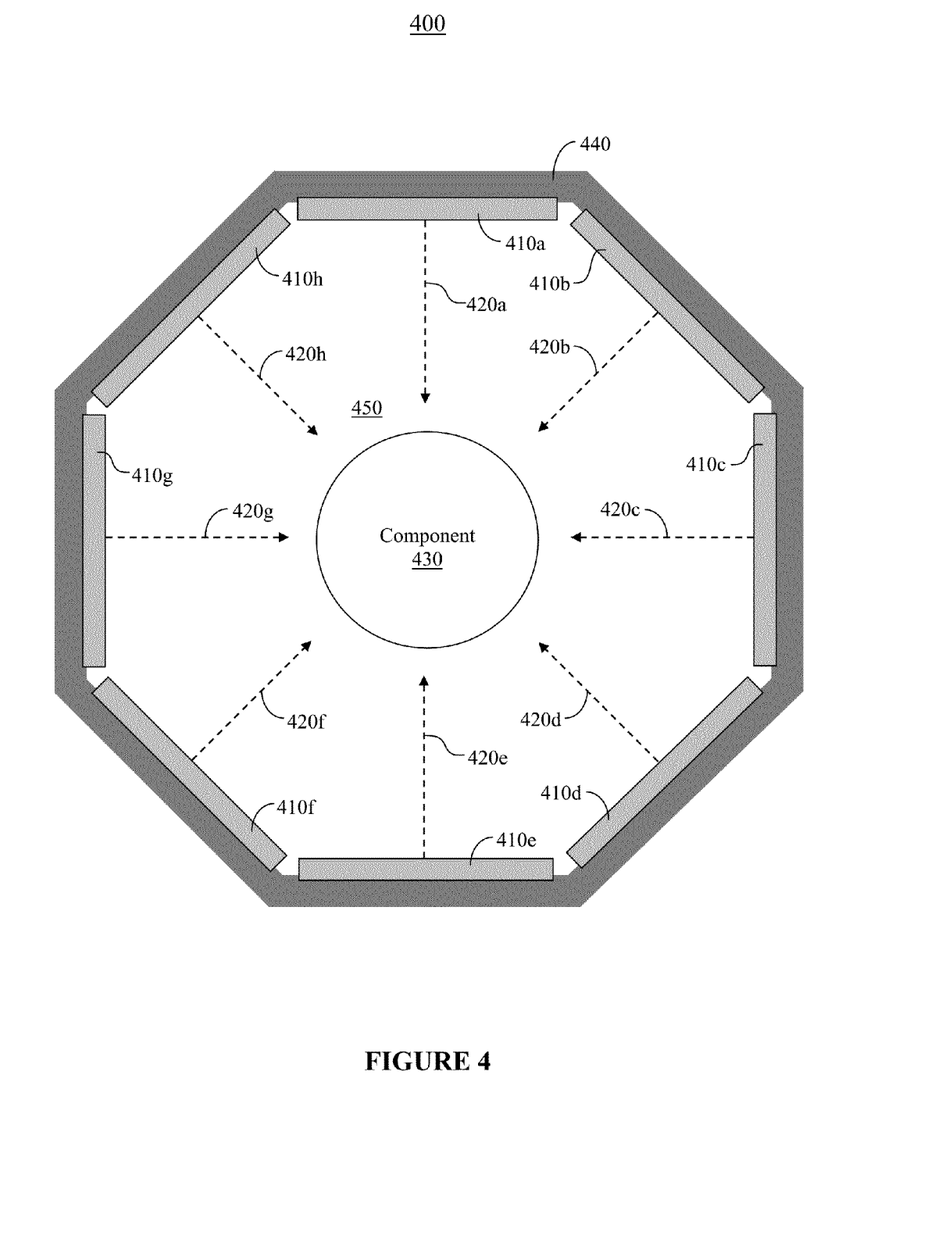
FIG. 4 shows an exemplary system for generating a plurality of electron flows in accordance with one embodiment of the present invention.

FIG. 4 shows exemplary system 400 for generating a plurality of electron flows in accordance with one embodiment of the present invention. As shown in FIG. 4, a plurality of electron flows (e.g., 420a, 420b, 420c, 420d, 420e, 420f, 420g, 420h, etc.) may be generated by a plurality of apparatuses (e.g., 410a, 410b, 410c, 410d, 410e, 410f, 410g, 410h, etc.). Component 430 may be introduced into the electron flows (e.g., by moving the component 430 to and/or through the electron flows, by moving the electron flows to and/or through component 430, etc.) to perform one or more operations (e.g., sterilization, purification, deodorization, cleaning, cross-linking, pest control, pathogen control, chain-scissioning associated with surface modification, waste treatment, etc.) associated with the component. In one embodiment, the plurality of electron flows may be toward the same component (e.g., 430) or otherwise intersect. Accordingly, embodiments of the present invention may increase the number and/or density of electrons used to perform at least one operation on a component (e.g., 430).

One or more of the plurality of apparatuses (e.g., 410a, 410b, 410c, 410d, 410e, 410f, 410g, 410h, etc.) may be implemented in accordance with (e.g., be similar to and/or operate similarly to) apparatus 110 in one embodiment. And in one embodiment, component 430 may be implemented in accordance with (e.g., be similar to and/or operate similarly to) component 130.

As shown in FIG. 4, the plurality of apparatuses (e.g., 410a, 410b, 410c, 410d, 410e, 410f, 410g, 410h, etc.) may be coupled with member 440. Member 440 may be used to secure and/or orient (e.g., point) each apparatus.

At least one vacuum source (e.g., similar to vacuum source 150) may be applied to the plurality of apparatuses (e.g., 410a, 410b, 410c, 410d, 410e, 410f, 410g, 410h, etc.), where at least two of the plurality of apparatuses may share a common vacuum source and/or where at least two of the plurality of apparatuses may utilize separate vacuum sources. At least one energy source (e.g., similar to energy source 140) may be applied to the plurality of apparatuses (e.g., 410a, 410b, 410c, 410d, 410e, 410f, 410g, 410h, etc.), where at least two of the plurality of apparatuses may share a common energy source and/or where at least two of the plurality of apparatuses may utilize separate energy sources.

In one embodiment, member 440 may form chamber or space 450 in which component 430 may flow, move or otherwise be located. For example, member 440 may be a pipe, duct, etc. allowing at least one operation (e.g., sterilization, purification, deodorization, cleaning, cross-linking, pest control, pathogen control, chain-scissioning associated with surface modification, waste treatment, etc.) to be performed on the component (e.g., 430) as the component moves through member 440. Accordingly, in one embodiment, system 440 may be incorporated in an existing system or device (e.g., a lavatory of an airplane or home, a water pipe in a home or business, a sewage treatment plant, etc.) to allow performance of at least one operation (e.g., sterilization, purification, deodorization, cleaning, cross-linking, pest control, pathogen control, chain-scissioning associated with surface modification, waste treatment, etc.) on a component (e.g., 430).

In one embodiment, a filter may be used to remove the by-products or other material produced as a result of the at least one operation associated with component 430. For example, component 430 may be passed through a filter to remove by-products or other material produced as a result of the at least one operation (e.g., sterilization, purification, deodorization, cleaning, etc.). In one embodiment, the filter may be coupled with member 440 and/or connected with chamber 450.

Although FIG. 4 shows a specific number of elements (e.g., apparatuses, electron flows, components, etc.), it should be appreciated that system 400 may include any number of elements in other embodiments. Additionally, although FIG. 4 shows a specific arrangement and configuration of elements, it should be appreciated that system 400 may include any arrangement and/or configuration of elements in other embodiments.

Figure 5:
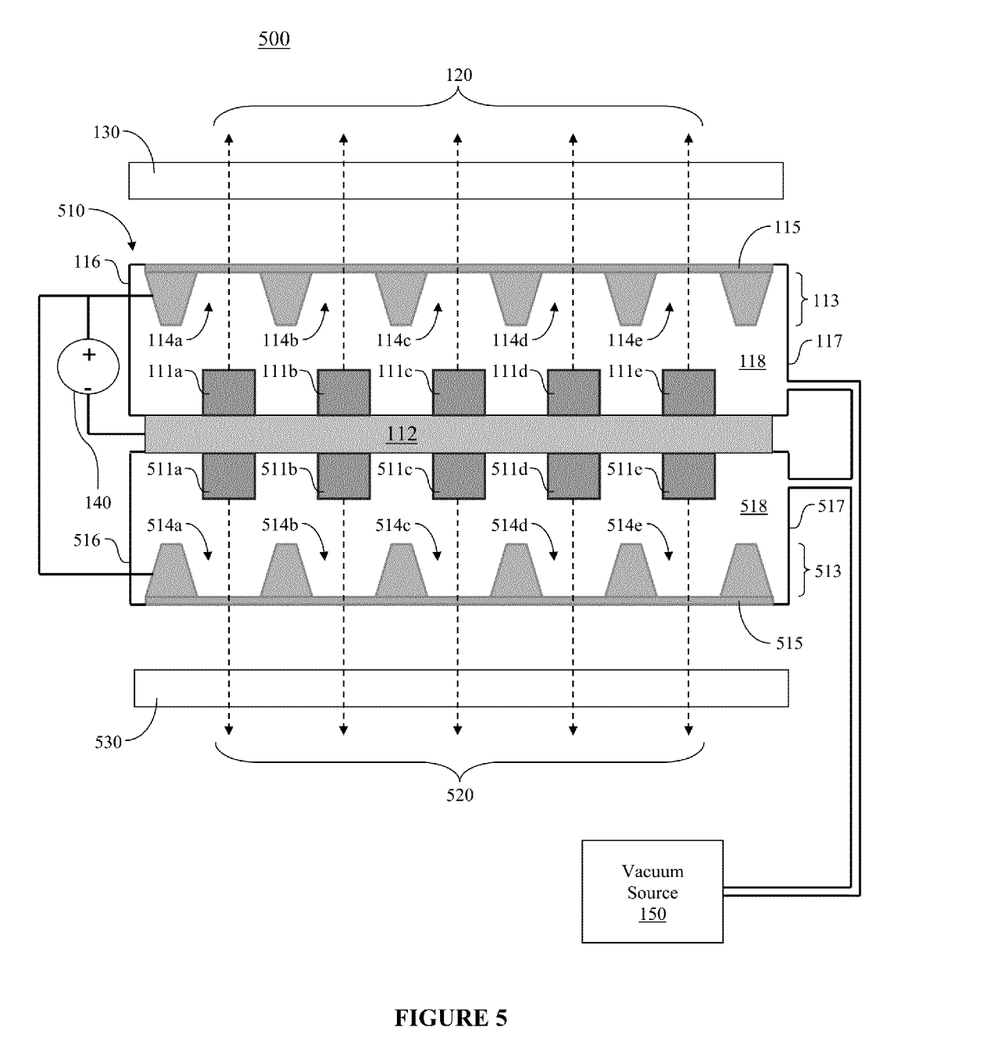
FIG. 5 shows an exemplary system for generating a plurality of electron flows toward or on a plurality of components in accordance with one embodiment of the present invention.

FIG. 5 shows exemplary system 500 for generating a plurality of electron flows toward or on a plurality of components in accordance with one embodiment of the present invention. As shown in FIG. 5, electrons flows 120 and 520 are emitted from apparatus 510 and directed toward or on components 130 and 530. The directions of the electron flows (e.g., 120 and 520) may be opposite one another in one embodiment. Each of the components (e.g., 130 and 530) may be introduced into the respective electron flows (e.g., by moving the components to and/or through the electron flows, by moving the electron flows to and/or through the components, etc.) to perform one or more operations associated with the components. The one or more operations may include sterilization, purification, deodorization, cleaning, cross-linking (e.g., for curing a paint, ink, coating, adhesive, polymer, etc.), pest control (e.g., in food products, other applications, etc.), pathogen control (e.g., in food products, other applications, etc.), chain-scissioning associated with surface modification, waste treatment, etc. As such, one or more operations may be more effectively performed (e.g., associated with a plurality of components) by using multiple groups of carbon nanotubes to emit electrons.

In one embodiment, electron flow 520 may be generated or emitted similarly to electron flow 120. For example, energy source 140 may be electrically coupled between substrate 112 and member 513 to allow extraction of electrons from a plurality of groups of carbon nanotubes (e.g., group 511a, group 511b, group 511c, group 511d, group 511e, etc.), where the plurality of groups of carbon nanotubes are aligned with a plurality of openings (e.g., opening 514a, opening 514b, opening 514c, opening 514d, opening 514e, etc.) defined by member 513. Membrane 515 may be disposed on or coupled with member 513 to allow the electrons of electron flow 520 to be transmitted from chamber 518 toward or onto component 530.

Membrane 515 may be electron permeable in one embodiment. For example, membrane 515 may allow electrons (e.g., of electron flow 520) to flow from chamber 518 toward component 530. Membrane 515 may be relatively thin (e.g., less than approximately 10 micrometers, less than approximately 3 micrometers, in the range of approximately 10 nanometers to approximately 10 micrometers, etc.) in one embodiment. Membrane 515 may be made from silicon nitride ($Si_3N_4$), silicon oxide, a combination of silicon nitride and silicon oxide (e.g., at least one silicon nitride layer and at least one silicon oxide layer, a material made of silicon nitride and silicon oxide, etc.), one or more other materials capable of transmitting electrons, etc.

As shown in FIG. 5, a vacuum may be applied to the groups of carbon nanotubes (e.g., group 511a, group 511b, group 511c, group 511d, group 511e, etc.) in one embodiment. For example, where the groups of carbon nanotubes are disposed in chamber 518, vacuum source 150 may apply a vacuum to chamber 518. Chamber 518 may be formed, in one embodiment, by layer or membrane 515, substrate 112, wall 516 and wall 517.

In one embodiment, the plurality of groups of carbon nanotubes of system 500 (e.g., group 111a, group 111b, group 111c, group 111d, group 111e, etc.) may be implemented in accordance with (e.g., be similar to and/or operate similarly to) the plurality of groups of carbon nanotubes of system 500 (e.g., group 511a, group 511b, group 511c, group 511d, group 511e, etc.). Member 513 may be implemented in accordance with (e.g., be similar to and/or operate similarly to) member 113 in one embodiment. In one embodiment, membrane 515 may be implemented in accordance with (e.g., be similar to and/or operate similarly to) membrane 115. Component 530 may be implemented in accordance with (e.g., be similar to and/or operate similarly to) component 130 in one embodiment.

In one embodiment, a filter may be used to remove the by-products or other material produced as a result of the at least one operation associated with component 130 and/or component 530. For example, component 130 and/or component 530 may be passed through a filter to remove by-products or other material produced as a result of the at least one operation (e.g., sterilization, purification, deodorization, cleaning, etc.). In one embodiment, the filter may be coupled with apparatus 510 and/or connected with a chamber in which component 130 and/or component 530 is located.

Although FIG. 5 shows vacuums in multiple chambers (e.g., 118 and 518) applied by the same vacuum source (e.g., 150), it should be appreciated that separate vacuum sources may be used to apply vacuums or otherwise alter the pressure within the chambers in other embodiments. Additionally, although FIG. 5 shows only one energy source (e.g., 140) for applying an electric potential to groups of carbon nanotubes (e.g., disposed on either side of substrate 112), it should be appreciated that more than one energy source may be used to apply an electric potential to a plurality of groups of carbon nanotubes (e.g., one energy source for the groups of carbon nanotubes disposed above substrate 112 and another energy source for the groups of carbon nanotubes disposed below substrate 112) in other embodiments.

Although FIG. 5 shows system 500 with a specific number of elements (e.g., groups of carbon nanotubes, members, membranes, openings defined by a member, vacuum sources, energy sources, etc.), it should be appreciated that system 500 may include a different number of elements in other embodiments. For example, energy source 140 may be implemented using two or more discrete energy sources (e.g., one to provide an electric potential between substrate 112 and member 113, another to provide an electric potential between substrate 112 and member 513, etc.). As another example, vacuum source 150 may be implemented using two or more discrete vacuum sources (e.g., one to apply a vacuum to chamber 118, another to apply a vacuum to chamber 518, etc.). Additionally, although FIG. 5 shows system 500 with a specific arrangement and configuration of elements (e.g., groups of carbon nanotubes, members, membranes, openings defined by a member, vacuum sources, energy sources, etc.), it should be appreciated that system 500 may include a different arrangement and/or configuration of elements in other embodiments.

Figure 6:
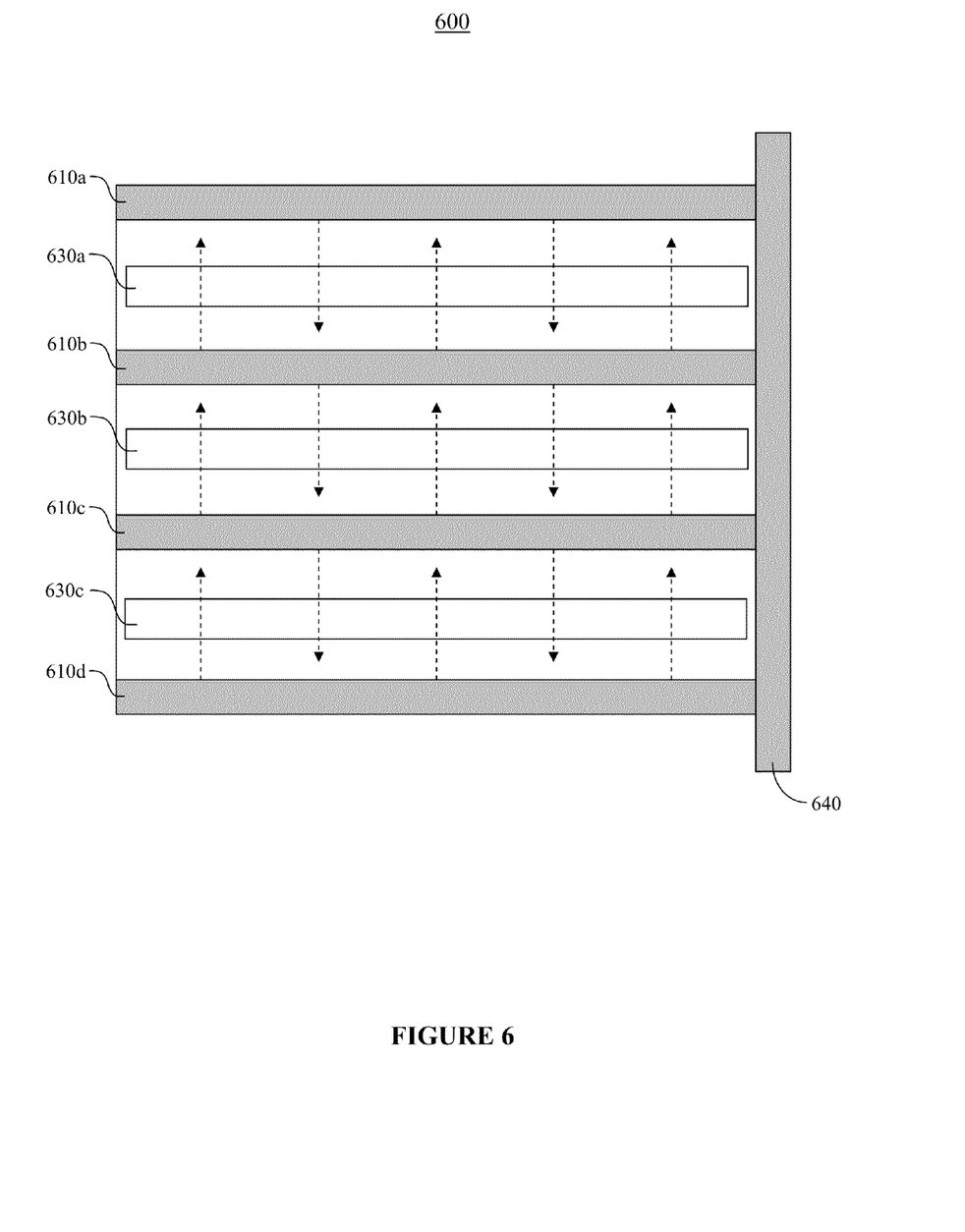
FIG. 6 shows an exemplary system including a plurality of apparatuses arranged to direct electrons toward or on a plurality of components in accordance with one embodiment of the present invention.

FIG. 6 shows exemplary system 600 including a plurality of apparatuses (e.g., 610*a*, 610*b*, 610*c* and 610*d*) arranged to direct electrons toward or on a plurality of components (e.g., 630*a*, 630*b* and 630*c*) in accordance with one embodiment of the present invention. As shown in FIG. 6, the plurality of components may be introduced into the electron flows (e.g., by moving the components to and/or through the electron flows, by moving the electron flows to and/or through the components, etc.) to perform one or more operations (e.g., sterilization, purification, deodorization, cleaning, cross-linking, pest control, pathogen control, chain-scissioning associated with surface modification, waste treatment, etc.) associated with the components. One or more of the apparatuses (e.g., 610*a*, 610*b*, 610*c*, 610*d*, etc.) may be implemented in accordance with (e.g., be similar to and/or operate similarly to) apparatus 110 and/or apparatus 510. Additionally, one or more of the components (e.g., 630*a*, 630*b*, 630*c*, etc.) may be implemented in accordance with (e.g., be similar to and/or operate similarly to) component 130 and/or component 530. In one embodiment, electrons may be emitted toward or on each component (e.g., 630*a*, 630*b*, 630*c*, some combination thereof, etc.) from a plurality of directions. In this manner, more electrons may be generated and emitted for performing one or more operations associated with a plurality of components (e.g., 630*a*, 630*b*, 630*c*, etc.).

As shown in FIG. 6, the plurality of apparatuses (e.g., 610*a*, 610*b*, 610*c*, 610*d*, etc.) may be coupled with member 640. Member 640 may be used to secure and/or orient (e.g., point) each apparatus. In one embodiment, the plurality of apparatuses may be spaced at a fixed distance (e.g., approximately on-half inch, one inch, two inches, or any other distance) and/or a plurality of distances (e.g., the distance a first pair of apparatuses may be different from the distance between another pair of apparatuses).

At least one vacuum source (e.g., similar to vacuum source 150) may be applied to the plurality of apparatuses (e.g., 610*a*, 610*b*, 610*c*, 610*d*, etc.), where at least two of the plurality of apparatuses may share a common vacuum source and/or where at least two of the plurality of apparatuses may utilize separate vacuum sources. At least one energy source (e.g., similar to energy source 140) may be applied to the plurality of apparatuses (e.g., 610*a*, 610*b*, 610*c*, 610*d*, etc.), where at least two of the plurality of apparatuses may share a common energy source and/or where at least two of the plurality of apparatuses may utilize separate energy sources.

In one embodiment, the plurality of apparatuses (e.g., 610*a*, 610*b*, 610*c*, 610*d*, etc.) alone or in combination with member 640 may form a channel, duct, etc. in which the components (e.g., 630*a*, 630*b*, 630*c*, etc.) may flow, move or otherwise be located. For example, the plurality of apparatuses alone or in combination with member 640 may form a channel, duct, etc. allowing at least one operation (e.g., sterilization, purification, deodorization, cleaning, cross-linking, pest control, pathogen control, chain-scissioning associated with surface modification, waste treatment, etc.) to be performed on the components as the components move with respect to the plurality of apparatuses and/or member 640.

In one embodiment, a filter may be used to remove the by-products or other material produced as a result of the at least one operation associated with a component of system 600 (e.g., component 630*a*, component 630*b*, component 630*c*, etc.). For example, one or more components (e.g., component 630*a*, component 630*b*, component 630*c*, etc.) may be passed through a filter to remove by-products or other material produced as a result of the at least one operation (e.g., sterilization, purification, deodorization, cleaning, etc.). In one embodiment, the filter may be coupled with at least one apparatus (e.g., 610*a*, 610*b*, 610*c*, etc.) and/or connected with a chamber in which at least one component (e.g., component 630*a*, component 630*b*, component 630*c*, etc.) is located.

Although FIG. 6 shows a specific number of elements (e.g., apparatuses, electron flows, components, etc.), it should be appreciated that system 600 may include any number of elements in other embodiments. Additionally, although FIG. 6 shows a specific arrangement and configuration of elements, it should be appreciated that system 600 may include any arrangement and/or configuration of elements in other embodiments.

Figure 7:
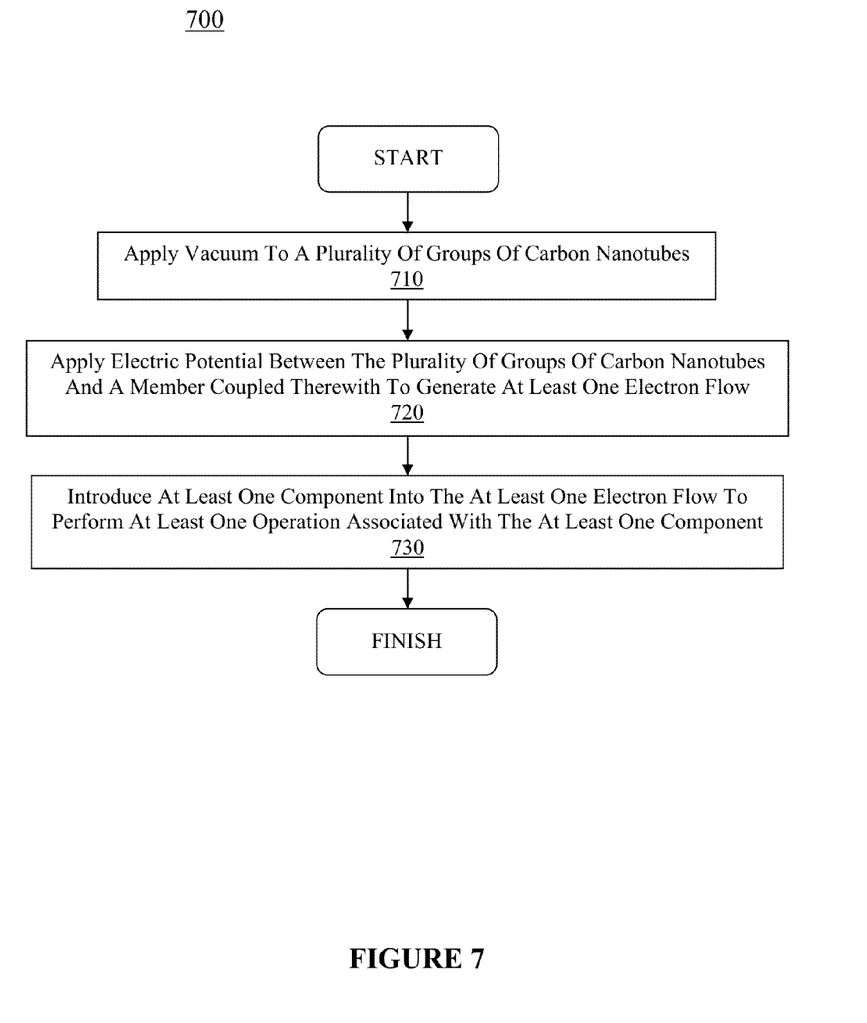
FIG. 7 shows a flowchart of an exemplary process for generating an electron flow in accordance with one embodiment of the present invention.

FIG. 7 shows a flowchart of exemplary process 700 for generating an electron flow in accordance with one embodiment of the present invention. As shown in FIG. 7, step 710 involves applying a vacuum to a plurality of groups of carbon nanotubes. For example, step 710 may involve using a vacuum source (e.g., 150) to apply a vacuum to a plurality of groups of carbon nanotubes (e.g., group 111*a*, group 111*b*, group 111*c*, group 111*d*, group 111*e*, group 511*a*, group 511*b*, group 511*c*, group 511*d*, group 511*e*, some combination thereof, etc.). The plurality of groups of carbon nanotubes may be disposed in one or more chambers (e.g., 118, 518, etc.) in one embodiment. And in one embodiment, the plurality of groups of carbon nanotubes may be coupled with or disposed on one or more sides of a single substrate (e.g., 112), a plurality of substrates (e.g., of separate apparatuses as shown in FIG. 4, FIG. 6, etc.), etc.

Step 720 involves applying an electric potential between the plurality of groups of carbon nanotubes (e.g., group 111a, group 111b, group 111c, group 111d, group 111e, group 511a, group 511b, group 511c, group 511d, group 511e, some combination thereof, etc.) and at least one member coupled therewith (e.g., member 113, member 513, etc.) to generate at least one electron flow (e.g., 120, 420a, 420b, 420c, 420d, 420e, 420f, 420g, 420h, 520, etc.). The electric potential may be applied in step 720 using at least one energy source (e.g., 140). In one embodiment, the electric potential may be applied in step 720 between a substrate (e.g., 112, a substrate that is electrically coupled to the plurality of groups of carbon nanotubes, etc.) and the at least one member. And in one embodiment, the electric potential applied in step 720 may be approximately 50,000 volts or less (e.g., at any value between approximately 50,000 volts and approximately 500 volts).

The at least one electron flow generated in step 720 may be directed through a plurality of openings defined by the at least one member (e.g., 113, 513, etc.) of one or more apparatuses (e.g., 110, 410a, 410b, 410c, 410d, 410e, 410f, 410g, 410h, 510, 610a, 610b, 610c, 610d, etc.). The at least one electron flow generated in step 720 may pass through at least one membrane (e.g., 115, 515, etc.) of one or more apparatuses (e.g., 110, 410a, 410b, 410c, 410d, 410e, 410f, 410g, 410h, 510, 610a, 610b, 610c, 610d, etc.), where the at least one membrane may be coupled with or disposed on the at least one member. In one embodiment, the at least one electron flow may include a first electron flow (e.g., 120) in a first direction and a second electron flow (e.g., 520) in a second direction, where the first and second electron flows may be opposite. And in one embodiment, the at least one electron flow may include a first electron flow (e.g., 420a) in a first direction and a second electron flow (e.g., 420b) in a second direction, where the first and second electron flows may be toward the same component (e.g., 430) or otherwise intersect.

As shown in FIG. 7, step 730 involves introducing at least one component (e.g., 130, 430, 530, 630a, 630b, 630c, etc.) into the at least one electron flow (e.g., generated in step 720) to perform at least one operation associated with the at least one component. The at least one operation may include sterilization, purification, deodorization, cleaning, cross-linking (e.g., for curing a paint, ink, coating, adhesive, polymer, etc.), pest control (e.g., in food products, other applications, etc.), pathogen control (e.g., in food products, other applications, etc.), chain-scissioning associated with surface modification, waste treatment, etc. The at least one component may be disposed in open air, a chamber filled with an inert gas (e.g., helium, argon, neon, etc.), a chamber filled with a fluid other than helium, in an environment of a different pressure than that of the plurality of groups of carbon nanotubes generating the at least one electron flow, in an environment of the same pressure as that of the plurality of groups of carbon nanotubes generating the at least one electron flow, etc.

In one embodiment, the at least one component (e.g., 430) may move with respect to or otherwise be disposed between or within a member (e.g., 440) used to secure and/or orient a plurality of apparatuses (e.g., 410a, 410b, 410c, 410d, 410e, 410f, 410g, 410h, etc.). And in one embodiment, the at least one component (e.g., 630a, 630b, 630c, etc.) may move with respect to or otherwise be disposed between or within a plurality of apparatuses (e.g., 610a, 610b, 610c, 610d, etc.) and/or a member (e.g., 640) used to secure the at least one component.

In the foregoing specification, embodiments of the invention have been described with reference to numerous specific details that may vary from implementation to implementation. Thus, the sole and exclusive indicator of what is, and is intended by the applicant to be, the invention is the set of claims that issue from this application, in the specific form in which such claims issue, including any subsequent correction. Hence, no limitation, element, property, feature, advantage, or attribute that is not expressly recited in a claim should limit the scope of such claim in any way. Accordingly, the specification and drawings are to be regarded in an illustrative rather than a restrictive sense.

What is claimed is:

1. An apparatus comprising:
    a plurality of groups of carbon nanotubes electrically coupled to a cathode substrate, wherein said plurality of groups of carbon nanotubes are operable to generate an electron flow;
    an anode member coupled with said plurality of groups of carbon nanotubes, wherein a plurality of openings is defined in said anode member, and wherein each opening of said plurality of openings is aligned with a respective group of said plurality of groups of carbon nanotubes; and
    a membrane disposed on said anode member and operable to transmit electrons of said electron flow, flowing through said plurality of openings in said anode member and through said membrane, onto a component.

2. The apparatus of claim 1, wherein said component is selected from a group consisting of a fluid, an object, a gas, a medical supply, a food, a surface, a paint, an ink, a coating, an adhesive, a polymer, and a waste.

3. The apparatus of claim 1, wherein said electrons are operable to perform at least one operation associated with said component, and wherein said at least one operation is selected from a group consisting of sterilization, purification, deodorization, cleaning, cross-linking, pest control, pathogen control, chain-scissioning associated with surface modification, and waste treatment.

4. The apparatus of claim 1, wherein said component comprises a fluid flowing adjacent to said membrane.

5. The apparatus of claim 1, wherein said plurality of groups of carbon nanotubes is disposed in a vacuum.

6. The apparatus of claim 1, wherein said plurality of groups of carbon nanotubes is operable to generate said electron flow in a first direction, and further comprising:
    a second plurality of groups of carbon nanotubes operable to generate a second electron flow in a second direction, and wherein said first and second directions are opposite;
    a second anode member coupled with said second plurality of groups of carbon nanotubes, wherein a second plurality of openings is defined in said second anode member, and wherein each opening of said second plurality of openings is aligned with a respective group of said second plurality of groups of carbon nanotubes; and
    a second membrane disposed on said second anode member and operable to transmit electrons of said second electron flow onto a second component, wherein said second electrons are operable to perform at least one operation associated with said second component.

7. The apparatus of claim 1, wherein said plurality of groups of carbon nanotubes is operable to generate said electron flow in a first direction toward said component, and further comprising:
    a second plurality of groups of carbon nanotubes operable to generate a second electron flow in a second direction toward said component;
    a second anode member coupled with said second plurality of groups of carbon nanotubes, wherein a second plurality of openings is defined in said second anode member, and wherein each opening of said second plurality of openings is aligned with a respective group of said second plurality of groups of carbon nanotubes; and a second membrane disposed on said second anode member and operable to transmit electrons of said second electron flow onto said component.

8. The apparatus of claim 1, wherein said membrane has a thickness in the range of approximately 10 nanometers to approximately 10 micrometers, and wherein said membrane comprises a material selected from the group consisting of silicon nitride and silicon oxide.

9. A system comprising:
a component;
an apparatus comprising:
a plurality of groups of carbon nanotubes operable to generate an electron flow;
an anode member coupled with said plurality of groups of carbon nanotubes, wherein a plurality of openings is defined in said anode member, and wherein each opening of said plurality of openings is aligned with a respective group of said plurality of groups of carbon nanotubes; and
a membrane disposed on said anode member and operable to transmit electrons of said electron flow onto said component; and
a vacuum source operable to apply a vacuum to said plurality of groups of carbon nanotubes.

10. The system of claim 9, wherein said component is selected from a group consisting of a fluid, an object, a gas, a medical supply, a food, a surface, a paint, an ink, a coating, an adhesive, a polymer, and a waste.

11. The system of claim 9, wherein said electrons are operable to perform at least one operation associated with said component, and wherein said at least one operation is selected from a group consisting of sterilization, purification, deodorization, cleaning, cross-linking, pest control, pathogen control, chain-scissioning associated with surface modification, and waste treatment.

12. The system of claim 9, wherein said component comprises a fluid flowing adjacent to said membrane.

13. The system of claim 9, wherein said apparatus further comprises:
a cathode substrate coupled with said plurality of groups of carbon nanotubes.

14. The system of claim 9, wherein said plurality of groups of carbon nanotubes is operable to generate said electron flow in a first direction, and wherein said apparatus further comprises:
a second plurality of groups of carbon nanotubes operable to generate a second electron flow in a second direction, and wherein said first and second directions are opposite;
a second anode member coupled with said second plurality of groups of carbon nanotubes, wherein a second plurality of openings is defined in said second anode member, and wherein each opening of said second plurality of openings is aligned with a respective group of said second plurality of groups of carbon nanotubes; and
a second membrane disposed on said second anode member and operable to transmit electrons of said second electron flow onto a second component, wherein said second electron are operable to perform at least one operation associated with said second component.

15. The system of claim 9, wherein said plurality of groups of carbon nanotubes is operable to generate said electron flow in a first, direction toward said component, and wherein said apparatus further comprises:
a second plurality of groups of carbon nanotubes operable to generate a second electron flow in a second direction toward said component;
a second anode member coupled with said second plurality of groups of carbon nanotubes, wherein a second plurality of openings is defined in said second anode member, and wherein each opening of said second plurality of openings is aligned with a respective group of said second plurality of groups of carbon nanotubes; and
a second membrane disposed on said second anode member and operable to transmit electrons of said second electron flow onto said component.

* * * * *